United States Patent [19]
Soto et al.

[11] Patent Number: 6,160,065
[45] Date of Patent: Dec. 12, 2000

[54] YTTRIUM CONTAINING METAL COMPLEXES AND OLEFIN POLYMERIZATION PROCESS

[75] Inventors: Jorge Soto; Jasson T. Patton, both of Midland, Mich.

[73] Assignee: The Dow Chemical Company, Midland, Mich.

[21] Appl. No.: 09/142,024

[22] PCT Filed: May 8, 1997

[86] PCT No.: PCT/US97/07849

§ 371 Date: Aug. 28, 1998

§ 102(e) Date: Aug. 28, 1998

[87] PCT Pub. No.: WO97/43294

PCT Pub. Date: Nov. 20, 1997

[51] Int. Cl.[7] .................................................. C08F 4/42
[52] U.S. Cl. ........................ 526/160; 526/126; 526/134; 526/135; 526/145; 526/170; 526/113; 526/943; 526/114; 502/152; 502/155; 502/154; 556/12

[58] Field of Search ...................... 526/126, 134, 526/135, 145, 160, 170, 113, 943, 114; 502/152, 154, 155; 556/12

[56] References Cited

U.S. PATENT DOCUMENTS

| 4,965,386 | 10/1990 | Watson et al. | 556/430 |
| 5,312,881 | 5/1994 | Marks et al. | 526/126 |
| 5,464,906 | 11/1995 | Patton et al. | 525/240 |

FOREIGN PATENT DOCUMENTS

| 0416815 | 3/1991 | European Pat. Off. . |
| 0634429 | 1/1995 | European Pat. Off. . |

*Primary Examiner*—David W. Wu
*Assistant Examiner*—L Choi

[57] ABSTRACT

Yttrium complexes of dibenzopyrolyl substituted cyclopentadienyl ligands are useful as ethylene polymerization catalysts to uniquely prepare low molecular weight ethylene polymers having a high degree of terminal vinyl unsaturation.

9 Claims, No Drawings

YTTRIUM CONTAINING METAL COMPLEXES AND OLEFIN POLYMERIZATION PROCESS

This invention relates to metal complexes and to addition polymerization catalysts formed therefrom that have improved catalytic performance. More particularly the present invention relates to an addition polymerization catalyst composition comprising a yttrium complex of a dibenzopyrrole substituted cyclopentadienyl or substituted cyclopentadienyl ligand. In addition, the present invention relates to a method of using the foregoing catalyst compositions in an addition polymerization process for polymerizing addition polymerizable monomers.

In EP-A-416,815 there are disclosed certain constrained geometry metal complexes and catalysts derived by reacting the metal complex with activating cocatalysts. Supported derivatives of such catalysts were prepared by contacting them with a support such as alumina, silica or $MgCl_2$. In U.S. Pat. No. 5,464,906 there are disclosed certain catalyst compositions comprising bridged Group 3 metal complexes, especially scandium containing complexes that were usefully employed as catalysts in addition polymerizations.

It would be desirable if there were provided an improved catalyst composition comprising a yttrium metal complex as well as an improved addition polymerization process utilizing such catalyst compositions.

As a result of investigations carried out by the present inventor there have now been discovered certain dibenzopyrrole substituted cyclopentadienyl complexes of yttrium corresponding to the formula:

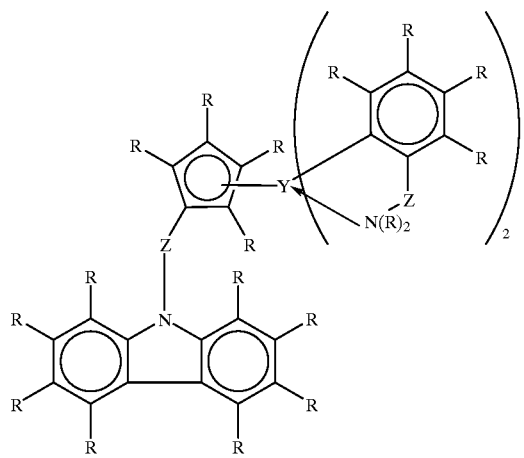

wherein
Y is yttrium;
R independently in each occurrence is selected from the group consisting of hydrogen, hydrocarbyl, silyl, or germyl, said R having up to 20 non-hydrogen atoms, or adjacent R groups are linked together thereby forming a fused ring system; and
Z is a divalent substituent of up to 50 non-hydrogen atoms having the formula, $-(ER'_2)_m-$, wherein E independently each occurrence is carbon, silicon or germanium, R' independently each occurrence is selected from the group consisting of hydrocarbyl, hydrocarbyloxy, silyl, and germyl of up to 20 atoms other than hydrogen, and m is an integer from 1 to 3, or a dimer, solvated adduct or chelated derivative of such complex.

In addition there is provided an improved method for polymerization of addition polymerizable monomers using a catalyst composition comprising one or more of the foregoing metal complexes. Such addition polymerization processes may be used to prepare polymers for use in making molded articles, films, sheets, foamed materials and in other industrial applications.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Preferred R groups in the foregoing formula include straight and branched alkyl radicals, cycloalkyl radicals, aryl radicals, alkyl-substituted cycloalkyl radicals, and alkyl-substituted aromatic radicals. In addition two or more such radicals may together form a fused ring system which may be saturated or unsaturated. Examples of the latter are indenyl-, tetrahydroindenyl-, fluorenyl-, and octahydrofluorenyl- groups. Additional preferred radicals include trimethylsilyl, triethylsilyl, ethyldimethylsilyl, methyldiethylsilyl, triphenylgermyl, and trimethylgermyl radicals.

Preferred cyclic π-bonded groups include, cyclopentadienyl, indenyl, fluorenyl, tetrahydroindenyl, tetrahydrofluorenyl, octahydrofluorenyl, and $C_{1-10}$ hydrocarbyl-substituted derivatives thereof. Most preferred cyclopentadienyl based groups are tetramethylcyclopentadienyl, 2-methylindenyl, 3-methylindenyl, 2,3-dimethylindenyl, 2,3,5,6-tetramethylindenyl, and 2,3,5,6,7-pentamethylindenyl. It is understood that when substituted with the divalent substituent Z, the foregoing L groups are the corresponding divalent derivatives of the specifically named groups substituted at a ring position with the Z ligand.

Preferred Z groups are dimethylsilanediyl, diphenylsilanediyl, methylisopropoxysilanediyl, methylphenylsilanediyl, methylene, and 1,2-ethanediyl.

Examples of highly preferred complexes according to the present invention correspond to the formula:

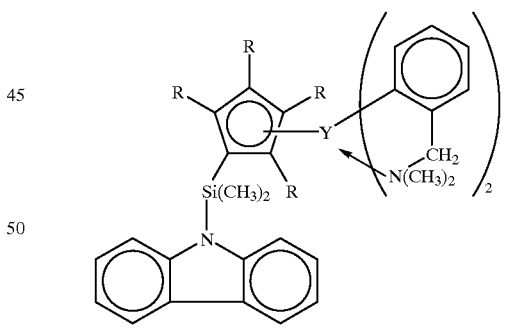

wherein.
R independently in each occurrence is selected from the group consisting of hydrogen, methyl, trimethylsilyl or adjacent R groups are linked together thereby forming an indenyl, 2-methylindenyl, 3-methylindenyl, 2,3-dimethylindenyl, 2,3,5,6-tetramethylindenyl, 2,3,5,6,7-pentamethylindenyl, 2-methyl-4-phenylindenyl, 2-methyl-4-naphthylindenyl, tetrahydroindenyl, fluorenyl, tetrahydrofluorenyl, or octahydrofluorenyl group.

The yttrium containing complexes are catalytically active without addition of an activating cocatalyst or use of an activation technique, however compounds that act as activating cocatalysts when combined with other metallocenes may be present in combination with the yttrium containing metal complexes of the invention without detrimental effect. Such activating cocatalysts are more fully described hereinafter.

Additional components of the catalyst composition include adjuvants to remove contaminants or catalyst poisons from the reaction mixture, to modify the polymerization kinetics, or to control polymer molecular weight. One such suitable adjuvant is a Group 13 organo compound, especially a trihydrocarbyl aluminum compound or a dihydrocarbylhydrocarbyloxy aluminum compound. An especially preferred adjuvant is triisobutyl aluminum. Such adjuvant is normally added to the reaction mixture in a molar ratio based on yttrium complex from 0.1:1 to 100:1, more preferably from 1:1 to 10:1.

The yttrium containing metal complexes are surprisingly active catalysts compared to even the corresponding complexes containing a pyrrole ligand in place of the dibenzopyrrole ligand. In addition, catalyst compositions comprising the foregoing yttrium containing metal complexes uniquely form a large percentage of desirably vinyl terminated, relatively low molecular weight, high ethylene content polymer. Because of the low comonomer incorporation such ethylene polymers generally are relatively highly crystalline. This trait can be utilized to advantage in a multistep reaction process to form interpolymers containing a highly crystalline ethylene polymer segment and different olefin polymer segments having a different crystalline structure, or an amorphous structure, or including different functionality such as aromatic functionality.

More particularly there may be provided a process for forming an interpolymer of ethylene and optionally one or more addition polymerizable comonomers comprising:

1) contacting a reaction mixture comprising ethylene with a first catalyst composition comprising a yttrium containing complex as previously disclosed to form a polymer solution comprising a vinyl terminated ethylene polymer, 2) contacting a second reaction mixture comprising the vinyl terminated ethylene polymer and at least one copolymerizable comonomer with a catalyst system to prepare an interpolymer thereof, and 3) recovering the resulting interpolymer.

The polymer solution resulting from the first reaction mixture may be what is utilized as the second reaction mixture thereby leading to a unified process for preparing the foregoing interpolymers. Thus, in a further embodiment of the invention, there is provided a process comprising:

1) contacting ethylene alone or a mixture of ethylene with one or more higher α-olefins or styrene with a catalyst composition comprising the foregoing yttrium containing metal complex to form a reaction mixture comprising a vinyl terminated, relatively low molecular weight, ethylene polymer, 2) subsequently or simultaneously, contacting the so formed reaction mixture, optionally with additional amounts of α-olefin monomer, with a second olefin polymerization catalyst, to form a polymer composition comprising the vinyl terminated, relatively low molecular weight, ethylene polymer; and recovering the resulting polymeric product.

By the foregoing technique, especially where the secondary polymerization utilizes a catalyst composition that is capable of incorporating large amounts of a relatively large α-olefin, there may be produced a polymer comprising both amorphous olefin copolymer segments and crystallizable, nonamorphous, high ethylene content, polymer segments. Due to the crystallinity of the nonamorphous segments such copolymers that result have higher service temperatures than conventional ethylene/α-olefin copolymers. Moreover, they may be produced in a single reactor or multiple reactors connected in series, from a mixture of ethylene and the appropriate α-olefin comonomer.

Suitable catalysts for copolymerization of ethylene and one or more higher α-olefins or styrene include high activity bis(cyclopentadienyl) metallocenes, especially zirconocenes, as well as monocyclopentadienyl Group 4 metal complexes known generically as constrained geometry catalysts. Such catalysts include any compound or complex of a metal of Groups 3–10 of the Periodic Table of the Elements capable of being activated to olefin insertion and polymerization by any suitable activator. Examples include Group 10 diimine derivatives corresponding to the formula:

The foregoing catalysts are disclosed by M. Brookhart, et al., in *J. Am. Chem. Soc.*, 118, 267–268 (1996) and *J. Am. Chem. Soc.*, 117, 6414–6415 (1995), as being active polymerization catalysts especially for polymerization of α-olefins, either alone or in combination with polar comonomers such as vinyl chloride, alkyl acrylates and alkyl methacrylates.

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by means of delocalized π electrons.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, a hydrogenated fused ring system, or a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl- substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471–480 (1995). Preferred boratabenzenes correspond to the formula:

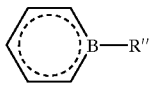

wherein R" is selected from the group consisting of hydrocarbyl, silyl, or germyl, said R " having up to 20 non-hydrogen atoms.

A suitable class of catalysts are transition metal complexes corresponding to the formula:

$$L_l MX_m X'_n X''_p, \text{ or a dimer thereof}$$

wherein:
L is an anionic, delocalized, π-bonded group that is bound to M, containing up to 50 non-hydrogen atoms, optionally two L groups may be joined together forming a bridged structure, and further optionally one L may be bound to X;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;
m is 0 or 1;
n is a number from 0 to 3;
p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two L groups. The latter complexes include those containing a bridging group linking the two L groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two L groups are compounds corresponding to the formula:

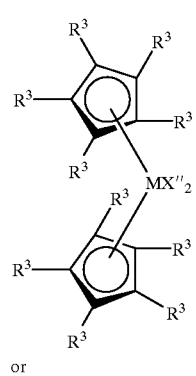

(I)

or

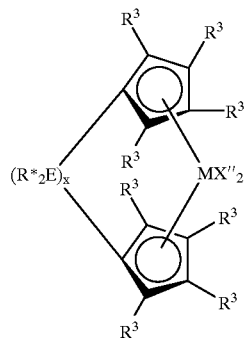

(II)

wherein:
M is zirconium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R_3$ groups together form a divalent derivative (that is, a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and R*, E and x are as previously defined.

The foregoing metal complexes are especially suited for the preparation of polymer segments having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: (dimethylsilyl-bis(cyclopentadienyl)), (dimethylsilyl-bis(methylcyclopentadienyl)), (dimethylsilyl-bis(ethylcyclopentadienyl)), (dimethylsilyl-bis(t-butylcyclopentadienyl)), (dimethylsilyl-bis(tetramethylcyclopentadienyl)), (dimethylsilyl-bis(indenyl)), (dimethylsilyl-bis(tetrahydroindenyl)), (dimethylsilyl-bis(fluorenyl)), (dimethylsilyl-bis(tetrahydrofluorenyl)), (dimethylsilyl-bis(2-methyl-4-phenylindenyl)), (dimethylsilyl-bis(2-methylindenyl)), (dimethylsilyl-cyclopentadienyl-fluorenyl), (dimethylsilyl-cyclopentadienyl-octahydrofluorenyl), (dimethylsilyl-cyclopentadienyl-tetrahydrofluorenyl), (1,1,2,2-tetramethyl-1,2-disilyl-bis-cyclopentadienyl), (1,2-bis(cyclopentadienyl)ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $L_lMX_mX'_nX''_p$, or a dimer thereof, wherein X is a divalent substituent of up to 50 non-hydrogen atoms that together with L forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

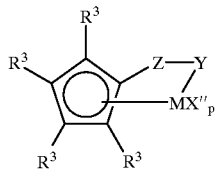

wherein:
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

p is one or two; and

Z is $SiR*_2$, $CR*_2$, $SiR*_2SiR*_2$, $CR*_2CR*_2$, $CR*{=}CR*$, $CR*_2SiR*_2$, or $GeR*_2$, wherein R* is as previously defined.

Illustrative of such Group 4 metal complexes that may be employed in the practice of the present invention include:

(tert-butylamido)(1,1-dimethyl-2,3,4,9,10-η-1,4,5,6,7,8-hexahydronaphthalenyl)dimethylsilane titaniumdimethyl, (tert-butylamido)(1,1,2,3-tetramethyl-2,3,4,9,10-η-1,4,5,6,7,8-hexahydronaphthalenyl)-dimethylsilanetitaniumdimethyl, (tert-butylamido)(tetramethyl-η⁵-cyclopentadienyl) dimethylsilanetitanium dibenzyl, (tert-butylamido)(tetramethyl-η⁵- cyclopentadienyl) dimethylsilanetitanium dimethyl, (tert-butylamido)(tetramethyl-η⁵-cyclopentadienyl)-1,2-ethanediyltitanium dimethyl, (tert-butylamido)(tetramethyl-η⁵-indenyl) dimethylsilanetitanium dimethyl, (tert-butylamido)(tetramethyl-η⁵-cyclopentadienyl) dimethylsilanetitanium (III) 2-(dimethylamino)benzyl;

(tert-butylamido)(tetramethyl-η⁵- cyclopentadienyl) dimethylsilanetitanium (III) allyl, (tert-butylamido)(tetramethyl-η⁵- cyclopentadienyl) dimethylsilanetitanium (IV) 2,4-dimethylpentadienyl, (tert-butylamido)(tetramethyl-η⁵-cyclopentadienyl) dimethylsilanetitanium (II) 1,4-diphenyl-1,3-butadiene, (tert-butylamido)(tetramethyl-η⁵-cyclopentadienyl) dimethylsilanetitanium (II) 1,3-pentadiene, (tert-butylamido)(2-methylindenyl) dimethylsilanetitanium (II) 1,4-diphenyl-1,3-butadiene, (tert-butylamido)(2-methylindenyl) dimethylsilanetitanium (II) 2,4-hexadiene, (tert-butylamido)(2-methylindenyl) dimethylsilanetitanium (IV) 2,3-dimethyl-1,3-butadiene, (tert-butylamido)(2-methylindenyl) dimethylsilanetitanium (IV)isoprene, (tert-butylamido)(2-methylindenyl) dimethylsilanetitanium (IV) 1,3-butadiene, (tert-butylamido)(2,3-dimethylindenyl) dimethylsilanetitanium (IV) 2,3-dimethyl-1,3-butadiene, (tert-butylamido)(2,3-dimethylindenyl) dimethylsilanetitanium (IV) isoprene (tert-butylamido)(2,3-dimethylindenyl) dimethylsilanetitanium (IV) dimethyl (tert-butylamido)(2,3-dimethylindenyl) dimethylsilanetitanium (IV) dibenzyl (tert-butylamido)(2,3-dimethylindenyl) dimethylsilanetitanium (IV) 1,3-butadiene, (tert-butylamido)(2,3-dimethylindenyl) dimethylsilanetitanium (II) 1,3-pentadiene, (tert-butylamido)(2,3-dimethylindenyl) dimethylsilanetitanium (II) 1,4-diphenyl-1,3-butadiene, (tert-butylamido)(2-methylindenyl) dimethylsilanetitanium (II) 1,3-pentadiene, (tert-butylamido)(2-methylindenyl) dimethylsilanetitanium (IV) dimethyl, (tert-butylamido)(2-methylindenyl) dimethylsilanetitanium (IV) dibenzyl, (tert-butylamido)(2-methyl-4-phenylindenyl) dimethylsilanetitanium (II) 1,4-diphenyl-1,3-butadiene, (tert-butylamido)(2-methyl-4-phenylindenyl) dimethylsilanetitanium (II) 1,3-pentadiene, (tert-butylamido)(2-methyl-4-phenylindenyl) dimethylsilanetitanium (II) 2,4-hexadiene, (tert-butylamido)(tetramethyl-$\eta^5$-cyclopentadienyl) dimethyl-silanetitanium (IV) 1,3-butadiene, (tert-butylamido)(tetramethyl-$\eta^5$-cyclopentadienyl) dimethyl-silanetitanium (IV) 2,3-dimethyl-1,3-butadiene, (tert-butylamido)(tetramethyl-$\eta^5$-cyclopentadienyl) dimethyl-silanetitanium (IV) isoprene, (tert-butylamido)(tetramethyl-$\eta^5$-cylopentadienyl) dimethyl-silanetitanium (II) 1,4-dibenzyl-1,3-butadiene, (tert-butylamido) (tetramethyl-$\eta^5$-cyclopentadienyl) dimethyl-silanetitanium (II) 2,4-hexadiene, (tert-butylamido)(tetramethyl-$\eta^5$-cyclopentadienyl) dimethyl-silanetitanium (II) 3-methyl-1,3-pentadiene, (tert-butylamido)(2,4-dimethylpentadien-3-yl)dimethyl-silanetitaniumdimethyl, (tert-butylamido)(6,6-dimethylcyclohexadienyl) dimethyl-sianetitaniumdimethyl, (tert-butylamido)(1,1-dimethyl-2,3,4,9,10-$\eta$-1,4,5,6,7,8-hexahydronaphthalen-4-yl-dimethylsilanetitaniumdimethyl, (tert-butylamido)(1,1,2,3-tetramethyl-2,3,4,9,10-$\eta$-1,4,5,6,7,8-hexahydronaphthalen-4-yl)-dimethylsilanetitaniumdimethyl (tert-butylamido)(tetramethyl-$\eta^5$-cyclopentadienyl methylphenyl-silanetitanium (IV) dimethyl, (tert-butylamido)(tetramethyl-$\eta^5$-cyclopentadienyl methylphenyl-silanetitanium (II) 1,4-diphenyl-1,3-butadiene, 1-(tert-butylamido)-2-(tetramethyl-$\eta^5$-cyclopentadienyl) ethanediyl-titanium (IV) dimethyl, and 1-(tert-butylamido)-2-(tetramethyl-$\eta^5$-cyclopentadienyl) ethanediyl-titanium (II) 1,4-diphenyl-1,3-butadiene.

Complexes containing two L groups including bridged complexes suitable for use in the present invention include:

bis(cyclopentadienyl)zirconium dimethyl,
bis(cyclopentadienyl)zirconium dibenzyl,
bis(cyclopentadienyl)zirconium methyl benzyl, bis(cyclopentadienyl)zirconium methyl phenyl,
bis(cyclopentadienyl)zirconium diphenyl,
bis(cyclopentadienyl)titanium-allyl, bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconium methyltrimethylsilyl,
bis(tetrahydroindenyl)zirconium methyltrimethylsilyl,
bis(pentamethylcyclopentadienyl) zirconiummethylbenzyl,
bis(pentamethylcyclopentadienyl)zirconiumdibenzyl,
bis(pentamethylcyclopentadienyl) zirconiummethylmethoxide,
bis(pentamethylcyclopentadienyl) zirconiummethylchloride,
bis(methylethylcyclopentadienyl)zirconiumdimethyl,
bis(butylcyclopentadienyl)zirconium dibenzyl,
bis(t-butylcyclopentadienyl)zirconiumdimethyl,
bis(ethyltetramethylcyclopentadienyl) zirconiumdimethyl,
bis(methylpropylcyclopentadienyl)zirconium dibenzyl,
bis(trimethylsilylcyclopentadienyl)zirconium dibenzyl,
dimethylsilyl-bis(cyclopentadienyl)zirconiumdimethyl,
dimethylsilyl-bis(tetramethylcyclopentadienyl)titanium-(III) allyl
dimethylsilyl-bis(t-butylcyclopentadienyl) zirconiumdichloride,
dimethylsilyl-bis(n-butylcyclopentadienyl) zirconiumdichloride,
(methylene-bis(tetramethylcyclopentadienyl)titanium (III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis(trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

Other catalysts, especially catalysts containing other Group 4 metals, will, of course, be apparent to those skilled in the art.

The complexes employed as secondary catalysts herein are rendered catalytically active by combination with an activating cocatalyst or by use of an activating technique. Suitable activating cocatalysts for use herein include polymeric or oligomeric alumoxanes, especially methylalumoxane, triisobutyl aluminum- modified methylalumoxane, or diisobutylalumoxane; strong Lewis acids, such as $C_{1-30}$ hydrocarbyl substituted Group 13 compounds, especially tri(hydrocarbyl)aluminum- or tri(hydrocarbyl)boron- compounds and halogenated derivatives thereof, having from 1 to 10 carbons in each hydrocarbyl or halogenated hydrocarbyl group, especially tris (pentafluorophenyl)borane; and nonpolymeric, inert, compatible, noncoordinating, ion forming compounds (including the use of such compounds under oxidizing conditions). A suitable activating technique is bulk electrolysis (explained in more detail hereinafter). Combinations of the foregoing activating cocatalysts and techniques may also be employed if desired. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651, EP-A-520,732, and WO93/23412

Suitable nonpolymeric, inert, compatible, noncoordinating, ion forming compounds useful as cocatalysts in one embodiment of the present invention comprise a cation which is a Bronsted acid capable of donating a proton, and a compatible, noncoordinating, anion, A⁻. Preferred anions are those containing a single coordination complex comprising a charge-bearing metal or metalloid core which anion is capable of balancing the charge of the active catalyst species (the metal cation) which is formed when the two components are combined. Also, said anion can be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are well known and many, particularly such compounds containing a single boron atom in the anion portion, are available commercially.

Preferably such cocatalysts may be represented by the following general formula:

$$(L^*-H)^+_d A^{d-}$$

wherein:

L* is a neutral Lewis base;

$(L^*-H)^+$ is a Bronsted acid;

$A^{d-}$ is a noncoordinating, compatible anion having a charge of d−, and d is an integer from 1 to 3.

More preferably d is one, that is, $A^{d-}$ is $A^-$.

Highly preferably, $A^-$ corresponds to the formula: $[BQ_4]^-$.

wherein:

B is boron in the +3 formal oxidation state; and

Q independently each occurrence is selected from hydride, dialkylamido, halide, alkoxide, aryloxide, hydrocarbyl, halocarbyl, and halosubstituted-hydrocarbyl radicals, said Q having up to 20 carbons with the proviso that in not more than one occurrence is Q halide.

In a more highly preferred embodiment, Q is a fluorinated $C_{1-20}$ hydrocarbyl group, most preferably, a fluorinated aryl group, especially, pentafluorophenyl.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate, methyldioctadecylammonium tetraphenylborate, triethylammonium tetraphenylborate, tripropylammonium tetraphenylborate, tri(n-butyl)ammonium tetraphenylborate, methyltetradecyloctadecylammonium tetraphenylborate, N,N-dimethylanilinium tetraphenylborate, N,N-diethylanilinium tetraphenylborate, N,N-dimethyl(2,4,6-trimethylanilinium) tetraphenylborate, trimethylammonium tetrakis(penta-fluorophenyl)borate, triethylammonium tetrakispentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl(2,4,6-trimethylanilinium) tetrakis(pentafluorophenyl)borate, trimethylammonium tetrakis(2,3,4,6-tetrafluorophenylborate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, and N,N-dimethyl-(2,4,6-trimethylanilinium) tetrakis-(2,3,4,6-tetrafluorophenyl)borate.

Dialkyl ammonium salts such as: di-(i-propyl)ammonium tetrakis(pentafluorophenyl)borate, and dicyclohexylammonium tetrakis(pentafluorophenyl)borate.

Tri-substituted phosphonium salts such as: triphenylphosphonium tetrakis(pentafluorophenyl)borate, tri(o-tolyl)phosphonium tetrakis(penta-fluorophenyl)borate, and tri(2, 6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}-C_{20}$ alkyl ammonium complexes, most specially methyldi(octadecyl)ammonium tetrakis(pentafluorophenyl)borate and ethyldi(tetradecyl)ammonium tetrakis(pentafluorophenyl)borate.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having charge e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion or silylium ion and a noncoordinating, compatible anion represented by the formula: ⓒ$^+$ A$^-$, wherein, ⓒ$^+$ is a $C_{1-20}$ carbenium ion or silylium ion; and A$^-$ is as previously defined.

A preferred carbenium ion is the trityl cation, that is triphenylcarbenium. A preferred silylium ion is triphenyisilylium.

The foregoing activating technique and ion forming cocatalysts are also preferably used in combination with a tri(hydrocarbyl)-aluminum compound having from 1 to 10 carbons in each hydrocarbyl group, an oligomeric or polymeric alumoxane compound, a di(hydrocarbyl)(hydrocarbyloxy)aluminum compound having from 1 to 20 carbons in each hydrocarbyl or hydrocarbyloxy group, or a mixture of the foregoing compounds, if desired. These aluminum compounds are usefully employed for their beneficial ability to scavenge impurities such as oxygen, water, and aldehydes from the polymerization mixture.

Suitable di(hydrocarbyl)(hydrocarbyloxy)aluminum compounds correspond to the formula $T^1{}_2AlOT^2$ wherein $T^1$ is $C_{3-6}$ secondary or tertiary alkyl, most preferably isopropyl, isobutyl or tert-butyl; and $T^2$ is a $C_{12-30}$ alkaryl radical or aralkyl radical, most preferably, 2,6-di(t-butyl)-4-methylphenyl, 2,6-di(t-butyl)-4-methyltolyl, 2,6-di(i-butyl)-4-methylphenyl, or 4-(3',5'-ditertiarybutyltolyl)-2,6-ditertiarybutylphenyl.

Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di(t-butyl)-4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The activating technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally, an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, A$^-$. Preferred supporting electrolytes are salts corresponding to the formula: G$^+$A$^-$; wherein:

G$^+$ is a cation which is nonreactive towards the starting and resulting complex, and A$^-$ is a noncoordinating, compatible anion.

Examples of cations, G$^+$, include tetrahydrocarbyl substituted ammonium or phosphonium cations having up to 40 nonhydrogen atoms. A preferred cation is the tetra-n-butylammonium cation.

During activation of the complexes by bulk electrolysis, the cation of the supporting electrolyte passes to the counter electrode and A$^-$ migrates to the working electrode to become the anion of the resulting oxidized product. Either the solvent or the cation of the supporting electrolyte is reduced at the counter electrode in equal molar quantity with the amount of oxidized metal complex formed at the working electrode.

Preferred supporting electrolytes are tetrahydrocarbylammonium salts of tetrakis(perfluoroaryl) borates having from 1 to 10 carbons in each hydrocarbyl group, especially tetra-n-butylammonium tetrakis(pentafluorophenyl) borate.

The molar ratio of catalyst/cocatalyst employed in the secondary polymerization preferably ranges from 1:10,000 to 100:1, more preferably from 1:5000 to 10:1, most preferably from 1:10 to 1:2.

In general, the catalysts used in the secondary polymerization can be prepared by combining the two components (metal complex and activator) in a suitable solvent at a temperature within the range from −100° C. to 300° C. or by generating the activated catalyst electrochemically as previously explained. The activated catalyst may be separately prepared prior to use by combining the respective components or prepared in situ by combination in the presence of the monomers to be polymerized. It is preferred to form the activated catalyst in situ due to the exceptionally high catalytic effectiveness of activated catalysts prepared in this manner. The catalyst and cocatalyst as well as activated catalyst are sensitive to both moisture and oxygen and should be handled and transferred in an inert atmosphere.

As previously mentioned, the secondary polymerization may further by performed in the presence of supported catalysts, formed by contacting the metal complex with a suitable substrate material. Especially suited substrates include alumina, silica or a prepolymer. Suitable supported catalyst systems are readily prepared by contacting the present metal complexes with the substrate optionally while subjecting to heating and/or reduced pressures. A Lewis base, especially a trialkylamine can be present to assist in the reaction between the support and any reactive functionality of the metal complexes if desired.

The support material may be in granular, agglomerated, pelletized, or any other physical form. Suitable materials include, but are not limited to, silicas available from Grace Davison (division of W.R. Grace & Co.) under the designations SD 3216.30, Davison Syloid 245, Davison 948 and Davison 952, and from Degussa AG under the designation Aerosil 812; and aluminas available from Akzo Chemicals Inc. under the designation Ketzen Grade B.

Supports suitable for the present invention preferably have a surface area as determined by nitrogen porosimetry using the B.E.T. method from 10 to 1000 $m^2/g$, and preferably from 100 to 600 $m^2/g$. The pore volume of the support, as determined by nitrogen adsorption, advantageously is between 0.1 and 3 $cm^3/g$, preferably from 0.2 to 2 $cm^3/g$. The average particle size is not critical, but typically is from 0.5 to 500 $\mu$m, preferably from 1 to 100 $\mu$m.

Both silica and alumina are known to inherently possess small quantities of hydroxyl functionality attached to the crystal structure. When used as a support, these materials are preferably subjected to a heat treatment and/or chemical treatment to reduce the hydroxyl content thereof. Typical heat treatments are carried out at a temperature from 30 to 1000° C. for a duration of 10 minutes to 50 hours in an inert atmosphere or under reduced pressure. Typical chemical treatments include contacting with Lewis acid alkylating agents such as trihydrocarbyl aluminum compounds, trihydrocarbylchlorosilane compounds, trihydrocarbylalkoxysilane compounds or similar agents. Preferred silica or alumina materials for use herein have a surface hydroxyl content that is less than 0.8 mmol hydroxyl groups per gram of solid support, more preferably less than 0.5 mmol per gram. The hydroxyl content may be determined by adding an excess of dialkyl magnesium to a slurry of the solid support and determining the amount of dialkyl magnesium remaining in solution via known techniques. This method is based on the reaction: S—OH+Mg(Alk)$_2$→S—OMg(Alk)+(Alk)H, wherein S is the solid support, and Alk is a $C_{1-4}$ alkyl group.

The support may be unfunctionalized (excepting for hydroxyl groups as previously disclosed) or functionalized by treating with a silane or chlorosilane functionalizing agent to attach thereto pendant silane —(Si-R)=, or chlorosilane —(Si-Cl)= functionality, wherein R is a $C_{1-10}$ hydrocarbyl group. Suitable functionalizing agents are compounds that react with surface hydroxyl groups of the support or react with the silicon or aluminum of the matrix. Examples of suitable functionalizing agents include phenylsilane, diphenylsilane, methylphenylsilane, dimethylsilane, diethylsilane, dichlorosilane, and dichlorodimethylsilane. Techniques for forming such functionalized silica or alumina compounds were previously disclosed in U.S. Pat. No. 3,687,920 and 3,879,368.

The support may also be treated with an aluminum component selected from an alumoxane or an aluminum compound of the formula $AlR^1{}_{x'}R^2{}_{y'}$, wherein $R^1$ independently each occurrence is hydride or R, $R^2$ is hydride, R or OR, x' is 2 or 3, y' is 0 or 1 and the sum of x' and y' is 3. Examples of suitable $R^1$ and $R^2$ groups include methyl, methoxy, ethyl, ethoxy, propyl (all isomers), propoxy (all isomers), butyl (all isomers), butoxy (all isomers), phenyl, phenoxy, benzyl, and benzyloxy. Preferably, the aluminum component is selected from the group consisting of aluminoxanes and tri($C_{1-4}$ hydrocarbyl)aluminum compounds. Most preferred aluminum components are aluminoxanes, trimethylaluminum, triethylaluminum, triisobutylaluminum, and mixtures thereof.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O)$_{m'}$, for a cyclic alumoxane, and $R_2Al$—O(—Al(R)—O)$_{m'}$—$AlR_2$, for a linear compound, wherein R is as previously defined, and m' is an integer ranging from 1 to 50, preferably at least 4. Alumoxanes are typically the reaction products of water and an alkylaluminum compound, which in addition to an alkyl group may contain halide or alkoxide groups. Reacting several different alkylaluminum compounds, such as for example trimethylaluminum and triisobutylaluminum, with water yields so-called modified or mixed alumoxanes. Preferred alumoxanes are methylalumoxane and methylalumoxane modified with minor amounts of $C_{2-4}$ alkyl groups, especially isobutyl groups. Alumoxanes generally contain minor to substantial amounts of starting alkylaluminum compound.

Particular techniques for the preparation of alumoxane type compounds by contacting an alkylaluminum compound with an inorganic salt containing water of crystallization are disclosed in U.S. Pat. No. 4,542,119. In a particular preferred embodiment an alkylaluminum compound is contacted with a regeneratable water-containing substance such as hydrated alumina, silica or other substance. This is disclosed in EP-A-338,044. Thus the alumoxane may be incorporated into the support by reaction of a hydrated alumina or silica material, which has optionally been functionalized with silane, sitoxane, hydrocarbyloxysilane, or chlorosilane groups, with a tri($C_{1-10}$ alkyl) aluminum compound according to known techniques The treatment of the support material in order to also include optional alumoxane or trialkylaluminum loadings involves contacting the same before, after or simultaneously with addition of the complex or activated catalyst hereunder with the alumoxane or trialkylaluminum compound, especially triethylaluminum or triisobutylaluminum. Optionally the mixture can also be heated under an inert atmosphere for a period and at a temperature sufficient to fix the alumoxane, trialkylaluminum compound, complex or catalyst system to the support. Optionally, the treated support component containing alumoxane or the trialkylaluminum compound may be subjected to one or more wash steps, using toluene or similar solvent, to remove alumoxane or trialkylaluminum not fixed to the support.

Besides contacting the support with alumoxane the alumoxane may be generated in situ by contacting an unhydrolyzed silica or alumina or a moistened silica or alumina with a trialkyl aluminum compound optionally in the presence of an inert diluent. Such a process is well known in the art, having been disclosed in EP-A-250,600, U.S. Pat. No. 4,912,075, and U.S. Pat. No. 5,008,228. Suitable aliphatic hydrocarbon diluents include pentane, isopentane, hexane, heptane, octane, isooctane, nonane, isononane, decane, cyclohexane, methylcyclohexane and combinations of two or more of such diluents. Suitable aromatic hydrocarbon diluents are benzene, toluene, xylene, and other alkyl or halogen substituted aromatic compounds. Most preferably, the diluent is an aromatic hydrocarbon, especially toluene. After preparation in the foregoing manner the residual hydroxyl content thereof is desirably reduced to a level less than 1.0 meq of OH per gram of support, by any of the previously disclosed techniques.

Suitable monomers for use herein are α-olefin monomers having from 2 to 100,000 carbon atoms and mixture thereof with addition polymerizable comonomers. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Preferred comonomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, and divinylbenzene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

In general, the polymerization may be accomplished at conditions well known in the prior art for Ziegler-Natta or Kaminsky-Sinn type polymerization reactions, such as temperatures from 0–250° C. and pressures from atmospheric to 1000 atmospheres (0.1 to 100 MPa). Suspension, solution, slurry, gas phase or other process conditions may be employed if desired. The support, if present, is preferably employed in an amount to provide a weight ratio of catalyst (based on metal):support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for polymerization via a solution process are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1,7-octadiene, 1-octene, 1-decene, styrene, divinylbenzene, ethylidenenorbornene, allylbenzene, vinyltoluene (including all isomers alone or in admixture), 4-vinylcyclohexene, and vinylcyclohexane. Mixtures of the foregoing are also suitable.

The yttrium containing catalyst compositions may be utilized in combination with at least one additional homogeneous or heterogeneous polymerization catalyst in the same or in separate reactors connected in series or in parallel to prepare polymer blends having desirable properties. A similar process making use of multiple catalysts is disclosed in WO 94/00500.

As further illustrative of the invention, one such polymerization process may comprise: contacting, optionally in a solvent, one or more a-olefins with a catalyst according to the present invention, in one or more continuous stirred tank or tubular reactors, connected in series or parallel, or in the absence of solvent, optionally in a fluidized bed gas phase reactor, and recovering the resulting reaction mixture, and thereafter continuing the polymerization in the presence of the secondary catalyst. Condensed monomer or solvent may be added to the gas phase reactor as is well known in the art.

The skilled artisan will appreciate that the invention disclosed herein may be practiced in the absence of any component which has not been specifically disclosed. In the following examples, unless stated to the contrary all parts and percentages are based on weight.

Example 1

Preparation of ($\eta^5$-tetramethylcyclopentadienyl) dimethyl(N-dibenzopyrolyl)-silaneyttrium bis(2-(N, N-dimethylaminomethyl)phenyl)

Syntheses of potassium dibenzopyrrole $K(NC_{12}H_8)$

A slurry of KH(9.91 g, 0.247 moles) in tetrahydrofuran (THF) (200 mL) was stirred as carbazole (41.3 g, 0.247 moles) was added slowly. The vigorous reaction was allowed to stir for 48 hours during which time the solution remained emerald green. After the reaction period the mixture was filtered and the volatile component removed resulting in a green solid. Several washes with pentane resulted in a pale green solid as the final product. Yield was 48.2 g, 95 percent.

Synthesis of (tetramethylcyclopentadienyl)dimethyl(N-dibenzopyrolyl)-silane $(C_5Me_4H)SiMe_2(NC_{12}H_8)$ $NaC_5Me_4H$ (3.11 g, 0.0216 moles) in THF (50 mL) was added to a solution of $Me_2SiCl_2$ (2.79 g, 0.0216 moles) in THF (50 mL) and allowed to stir for 3 hours. K(NC$_{12}$H8) in THF (50 mL) was then added slowly and the mixture allowed to stir for 16 hours. After the reaction period the volatile components were removed and the product extracted from the remainder with pentane. Removal of the pentane resulted in the isolation of the product as a pale yellow paste (6.94 g, 93 percent yield. Product identity was confirmed by $^1H$ NMR and $^{13}C$ NMR.

Synthesis of yttrium tris(2-(N,N-dimethylaminomethyl) phenyl) $Y(C_6H_4\text{-o-}CH_2NMe_2)_3$ $YCl_3(THF)_3$ (10.0 g, 0.0243 moles) and $Li(C_6H_4\text{-o-}CH_2NMe_2)$ (10.29 g, 0.0729 moles) was stirred in diethyl ether (300 mL) for 20 hours. After the reaction period the volatile materials were removed and the residue extracted with toluene and filtered after which the volatile materials were again stripped off. The brown solid was then washed with cold diethylether (3×20 mL) resulting in a fine white powder (8.10 g, 68 percent yield) $^1H$ NMR $(C_6D_6)$: 2.07(s, 6H), 3.44 (s, 2H), 6.94–7.36 (m, 3H), 8.19 (d, $^1J(H\text{—}H)$6.6 Hz. $^{13}C$ NMR $(C_6D_6)$: 45.98, 69.81, 124.83, 125.26, 125.76, 138.66, 146.78, 186.88 (d, $^1J(Y\text{—}C)$43.5 Hz).

Synthesis of ($\eta^5$-tetramethylcyclopentadienyl)dimethyl(N-dibenzopyrolyl)silaneyttrium bis(2-(N,N-dimethylaminomethyl)phenyl)

$Y(C_6H_4\text{-o-}CH_2NMe_2)_3$ (1.51 g, 0.00307 moles) and $(C_5Me_4H)SiMe_2(NC_{12}H_8)$ (1.06 g, 0.00307 moles) were heated in THF (100 mL) at 45° C. for 5 hours and then allowed to stir at room temperature for 48 hours. After the reaction period all volatile materials were removed. The resulting residue was washed several times with pentane at room temperature using a flip-frit apparatus. The product was isolated as a fine white powder (1.22 g, 57 percent yield). $^1H$ NMR $(C_6D_6)$: 0.35 (s, 3H), 0.92 (s, 3H), 1.70 (s, 3H), 1.94 (s, 6H), 2.03 (s 6H), 2.09 (s, 3H, 2.24 (s, 6H), 2.89 (d, $^1J(H\text{—}H)$14.1 Hz, 2H), 3.85 (d, $^1J(H\text{—}H)$14.4 Hz, 2H), 6.75 (d, $^1J(H\text{—}H)$8.0 Hz, 2H), 6.93 (d, $^1J(H\text{—}H)$7.1 Hz, 2H), 7.23(m, 8H). 7.77 (d, $^1J(H\text{—}H)$6.4 Hz, 2H), 8.03 ) (d, $^1$J(H—H)7.4 Hz, 2H). $^{13}$C NMR (C$_6$D$_6$): 2.37, 4.29, 11.58, 12.07. 14.73, 14.74, 45.30, 46.59, 69.96, 114,09, 119.54, 120.10, 124.95, 125.07, 125.60, 125.70, 126.91, 127.21, 138.63, 145.04, 146.08, 185.89 (d, $^1$J(Y—C)41.2 Hz).

Polymerization using (η$^5$-tetramethylcyclopentadienyl) dimethyl(N-dibenzopyrolyl)silaneyttrium bis(2-(N,N-dimethylaminomethyl)phenyl)

A nitrogen purged, two liter Parr reactor was charged with 700 g of mixed alkanes solvent and 150 g of 1-octene comonomer. Hydrogen was added as a molecular weight control agent by differential pressure expansion from an ~75 ml addition tank at 25 psi (170 kPa). The reaction mixture was stirred and heated to the polymerization temperature of 125° C. and saturated with ethylene at 325 psig (2.2 MPa). 10.0 μmol of (η$^5$-tetramethylcyclopentadienyl)-dimethyl(N-dibenzopyrolyl)silane-yttrium bis(2-(N, N-dimethylamino-methyl)phenyl) (as a 0.005M solution in toluene) was injected into the reactor. The polymerization conditions were maintained for 12 minutes with ethylene on demand. The resulting solution was removed from the reactor into a nitrogen purged container. The polymer formed was dried in a vacuum oven set at 120° C. for 20 hours yielding essentially pure ethylene homopolymer. The reaction was repeated twice more for a total of three runs. Average yield was 71.8 g. Average melt index (I$_2$) was 21.7 dg/min. Average Mw was 50,600. average Mw/Mn was 5.1. Average end group composition determined by $^{13}$C NMR was 68 mole percent olefin, of which on average 95 mole percent was vinylic unsaturation.

EXAMPLE 2

Preparation of Segmented Olefin Copolymer

The polymerization conditions of Example 1 were substantially repeated using Isopar E mixed aliphatic solvent (solv.) and a mixture of ethylene and 1-butene to prepare during a first reaction period a first reaction mixture comprising a vinyl terminated high ethylene content macromonomer, adding a second olefin polymerization catalyst to the reaction mixture and continuing polymerization for a second reaction period, and recovering the resulting copolymer containing product. During approximately the last 3 minutes of the first reaction period the reactor temperature was adjusted to the second reaction temperature before addition of the second catalyst composition. Thereafter the reaction temperature was maintained at the second reaction temperature. $^{13}$C NMR analysis of the unseparated product indicated the presence of long chain branches in the resulting polymer product due to copolymerization of the vinyl terminated high ethylene content macromonomer. Reaction conditions and yield are provided in Table 1.

What is claimed is:

1. A metal complex corresponding to the formula:

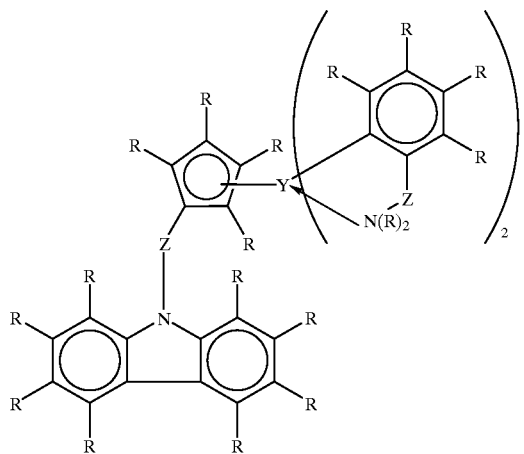

wherein
Y is yttrium;
R independently in each occurrence is selected from the group consisting of hydrogen, hydrocarbyl, silyl, and germyl, said R having up to 20 non-hydrogen atoms, or adjacent R groups are linked together thereby forming a fused ring system; and
Z is a divalent substituent of up to 50 non-hydrogen atoms having the formula, $-(ER'_2)_{m-}$, wherein E independently each occurrence is carbon, silicon or germanium, R' independently each occurrence is selected from the group consisting of hydrocarbyl, hydrocarbyloxy, silyl, and germyl of up to 20 atoms other than hydrogen, and m is an integer from 1 to 3, or a dimeric derivative, solvated adduct or chelated derivative thereof.

2. A metal complex according to claim 1 wherein R independently each occurrence is a straight or branched alkyl radical, a cycloalkyl radical, an aryl radical, an alkyl-substituted cycloalkyl radical, an alkyl-substituted aromatic radical or two or more such radicals together form a saturated or unsaturated fused ring system.

3. A metal complex according to claim 1 wherein the cyclic π-bonded group is cyclopentadienyl, indenyl, fluorenyl, tetrahydroindenyl, tetrahydrofluorenyl, octahydrofluorenyl, or a C$_{1-10}$ hydrocarbyl-substituted derivative thereof.

4. A metal complex according to claim 1 wherein the cyclic π-bonded group is tetramethylcyclopentadienyl, 2-methylindenyl, 3-methylindenyl, 2,3-dimethylindenyl,

TABLE 1

| Ex. | solv. (g) | temp 1 ° C. (min.) | temp 2 ° C. (min.) | C$_4$H$_8$ g | H$_2$ kPa | C$_2$H$_4$ MPa | 1C$^1$ μmol | TIBA$^2$ μmol | 2C$^3$ μmol | Yield g |
|---|---|---|---|---|---|---|---|---|---|---|
| 2 | 745 | 150(8) | 110(5) | 51 | 0 | 1.7 | 10 | 10 | 8 | 53.4 |
| 3 | 753 | 150(21) | 110(14) | 20 | 0 | 1.7 | 10 | 10 | 8 | 48.5 |
| 4 | 700 | 150(10) | 105(2) | 68 | 70 | 1.0 | 20 | 30 | 10 | 20.9 |
| 5 | 860 | 160(12) | 110(4) | 0 | 70 | 1.5 | 7 | 0 | 4 | 19.5 |

$^1$First catalyst composition: (η$^5$-tetramethylcyclopentadienyl)-dimethyl(N-dibenzopyrolyl)-silaneyttrium bis(2-(N,N-dimethylamino-methyl)phenyl) (as a 0.005M solution in toluene)
$^2$triisobutyl aluminum
$^3$Second catalyst composition: (η$^5$-tetramethylcyclopentadienyl)-dimethyl(N-t-butylamido) silanetitanium dimethyl + tris(pentafluorophenyl)borane 1:1 in toluene 2,3,5,6-tetramethylindenyl, or 2,3,5,6,7-pentamethylindenyl.

5. A metal complex according to claim 1 wherein Z independently each occurrence is dimethylsilanediyl, diphenylsilanediyl, methylisopropoxysilanediyl, methylphenylsilanediyl, methylene, or 1,2-ethanediyl.

6. A metal complex according to claim 1 corresponding to the formula:

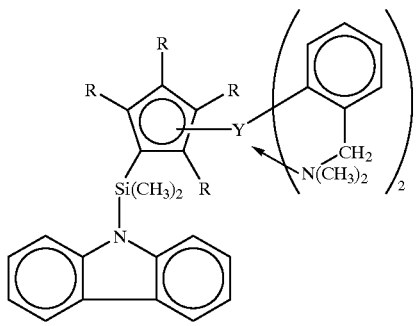

wherein:
R independently in each occurrence is selected from the group consisting of hydrogen, methyl, and trimethylsilyl or adjacent R groups are linked together thereby forming an indenyl, 2-methylindenyl, 3-methylindenyl, 2,3-dimethylindenyl, 2,3,5,6-tetramethylindenyl, 2,3,5,6,7-pentamethylindenyl, 2-methyl-4-phenylindenyl, 2-methyl-4-naphthylindenyl, tetrahydroindenyl, fluorenyl, tetrahydrofluorenyl, or octahydrofluorenyl group.

7. A process for polymerizing ethylene comprising contacting a reaction mixture comprising ethylene with a catalyst composition comprising a metal complex according to any of claims 1 to 6.

8. A process for forming an interpolymer of ethylene and optionally one or more addition polymerizable comonomers comprising:
1) contacting a reaction mixture comprising ethylene with a first catalyst composition comprising a metal complex according to any of claims 1 to 6 to form a polymer solution comprising a vinyl terminated ethylene polymer, 2) contacting a second reaction mixture comprising the vinyl terminated ethylene polymer and at least one copolymerizable comonomer with a catalyst system to prepare an interpolymer thereof, and 3) recovering the resulting interpolymer.

9. A process according to claim 8 wherein in step 2) the catalyst is derived from a metal complex corresponding to the formula:

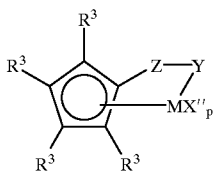

wherein:
M is titanium or zirconium in the +2, +3, or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

p is one or two; and

Z is $SiR^*_2$, $CR^*_2$, $SiR^*_2SiR^*_2$, $CR^*_2CR^*_2$, $CR^*{=}CR^*$, $CR^*_2SiR^*_2$, or $GeR^*_2$, wherein R* independently each occurrence is hydrogen or is selected from the group consisting of silyl, hydrocarbyl, hydrocarbyloxy and combinations thereof, said R* having up to 30 carbon or silicon atoms.

* * * * *